United States Patent [19]

Yoshida et al.

[11] Patent Number: 5,580,740
[45] Date of Patent: Dec. 3, 1996

[54] ANTIHUMAN PULMONARY ADENOCARCINOMA MONOCLONAL ANTIBODY

[75] Inventors: Hajime Yoshida, Kanagawa; Kenya Shitara, Tokyo, both of Japan

[73] Assignee: Kyowa Hakko Kogyo Co., Ltd., Japan

[21] Appl. No.: 422,660

[22] Filed: Apr. 14, 1995

Related U.S. Application Data

[63] Continuation of Ser. No. 191,147, Feb. 3, 1994, abandoned, which is a continuation of Ser. No. 93,145, Jul. 19, 1993, abandoned, which is a continuation of Ser. No. 829,529, Feb. 3, 1982, abandoned, which is a continuation of Ser. No. 693,039, Apr. 30, 1991, abandoned, which is a continuation of Ser. No. 470,633, Jan. 26, 1990, abandoned, which is a continuation of Ser. No. 172,795, Mar. 28, 1988, abandoned.

[51] Int. Cl.$^6$ .................... G01N 33/574; C07K 16/00
[52] U.S. Cl. .................... 435/7.23; 435/71; 435/70.21; 435/172.2; 435/240.27; 436/63; 436/64; 436/548; 530/387.1; 530/387.7; 530/395
[58] Field of Search .................... 435/7.1, 7.23, 435/172.2, 70.21, 240.27, 810; 436/64, 63, 548, 813, 808; 530/387.1, 395, 808, 828, 387.7

[56] References Cited

FOREIGN PATENT DOCUMENTS

| 0156578 | 3/1985 | European Pat. Off. . |
| 0218257 | 4/1987 | European Pat. Off. . |
| 0252769 | 1/1988 | European Pat. Off. . |

OTHER PUBLICATIONS

Varki et al, Cancer Research 44, pp. 681–687, Feb. 1984.
Edwards et al, Cancer Research 46, pp. 1306–1317, Mar. 1986.
Raddsevich et al, Cancer Research 45, pp. 5808–5812, Nov. 1985.
Lee et al, Cancer Research 45, pp. 5813–5817, Nov. 1985.

*Primary Examiner*—Christine M. Nucker
*Assistant Examiner*—Laurie Scheiner
*Attorney, Agent, or Firm*—Nixon & Vanderhye

[57] ABSTRACT

An antihuman pulmonary adenocarcinoma monoclonal antibody ALC-390 and a process for producing thereof are disclosed. This monoclonal antibody, which belongs to IgG class and is reactive with human pulmonary adenocarcinoma cell membranes and recognizes protein as the antigen, is highly useful in the pathological diagnosis of pulmonary adenocarcinoma and in the treatment of the same.

3 Claims, 5 Drawing Sheets

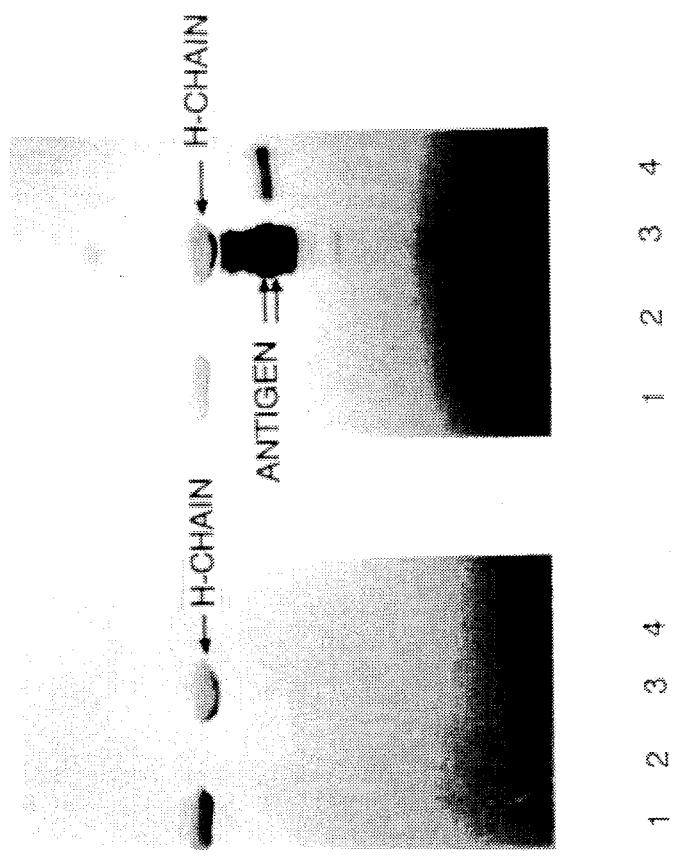
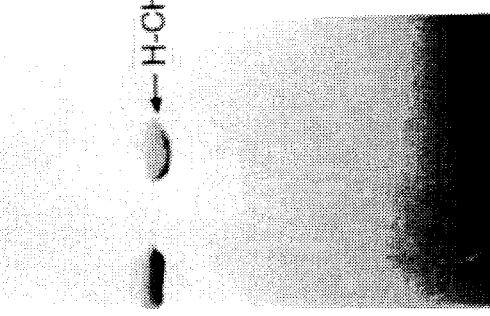
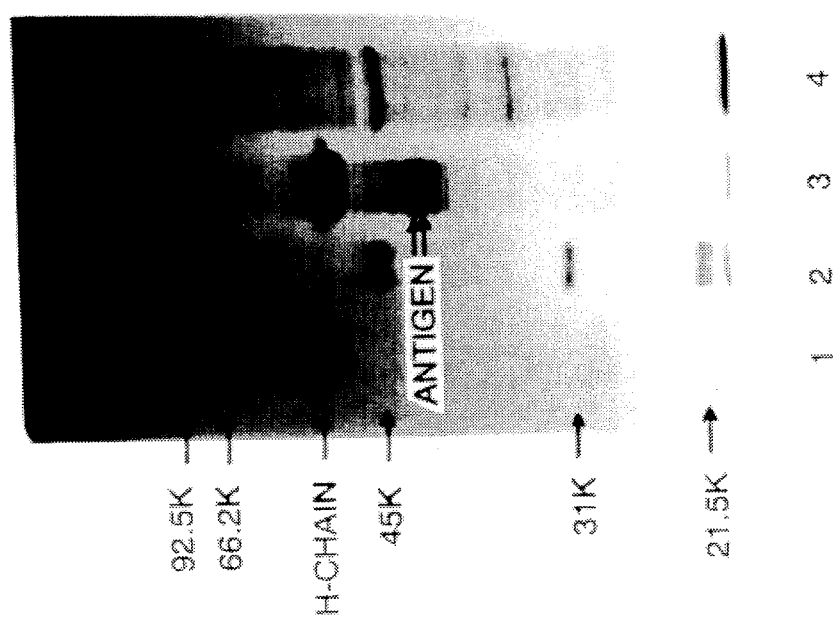

ANTIHUMAN PULMONARY ADENOCARCINOMA MONOCLONAL ANTIBODY

This is a continuation of application Ser. No. 08/191,147, filed Feb. 3, 1994, now abandoned, which is a continuation of 08/093,145 filed Jul. 19, 1993, now abandoned, which is a continuation of 07/829,529 filed Feb. 3, 1992, now abandoned, which is a continuation of 07/693,039 filed Apr. 30, 1991, now abandoned, which is a continuation of 07/470,633 filed Jan. 26, 1990, now abandoned, which is a continuation of 07/172,795 filed Mar. 28, 1988, now abandoned.

FIELD OF THE INVENTION

This invention relates to a monoclonal antibody ALC-390, which belongs to the IgG class and is reactive to human pulmonary adenocarcinoma and recognizes protein as the antigen, as well as processes for detecting and treating pulmonary adenocarcinoma with the use of the same. The present invention is available in the pathological diagnosis and treatment of pulmonary adenocarcinoma and thus useful in the field of diagnostic and therapeutic agents.

BACKGROUND OF THE INVENTION

Although it seems that there is no excellent tumor marker for lung cancer, we have developed a process for efficiently producing an antihuman pulmonary adenocarcimona monoclonal antibody by using human normal lung tolerant mice (cf. JP-A-60-190721 corresponding to EP-A-0156578) (the term "JP-A" used herein means an unexamined published Japanese patent application.) and thus established antihuman pulmonary adenocarcinoma monoclonal antibodies useful for serodiagnosis of pulmonary adenocarcinoma including SLC-1 (cf. JP-A-61-234357), ALC-1 (cf. JP-A-61-234358), ALC-186 (cf. JP-A-62-80558, JP-A-62-83898 corresponding to EP-A-0218257) and ALC-454 (cf. JP-A-63-19561 corresponding to EP-A-0252769). However, each of these monoclonal antibodies, which would recognize an antigen released in the serum of a patient suffering from lung cancer, is not always suitable for the cytological or histlogical diagnosis or treatment of this disease, though it is useful in the serodiagnosis thereof. Namely, a monoclonal antibody which recognized not a released antigen but rather a cancer cell membrane surface antigen is preferable for these purposes.

SUMMARY OF THE INVENTION

As described above, no monoclonal antibody to date is known which is highly specific to a pulmonary adenocarcinoma cell membrane and reacts with it at a high ratio. Thus, it is highly advantageous from diagnostic and therapeutic viewpoints to establish a monoclonal antibody highly specific to lung cancer cell membranes.

We have found that the monoclonal antibody ALC-390, which is produced by a hybridoma established by using a human pulmonary adenocarcinoma membrane component as an immunogen, is highly specific to a pulmonary adenocarcinoma cell membrane and is thus remarkably useful in the pathological diagnosis and treatment of pulmonary adenocarcinoma.

BRIEF DESCRIPTION OF THE DRAWING

In FIG. 1, o—o shows a result of treatment with neuraminidase (0.1 U/ml); △—△ shows a result of treatment with α-L-fucosidase (0.1 U/ml); ■—■ shows a result of treatment with trypsin (0.25 w/v %); □—□ shows a result of treatment with protease (10 U/ml); and ●—● shows a result of treatment with NaIO$_4$ (50 mM).

In FIG. 5, ●—● shows reactivity of ALC-390 with human normal lung tissue; o—o shows that with human pulmonary adenocarcinoma; △—△ shows that with human pulmonary adenocarcinoma cell line PC-9-derived tumor tissue; and ▲—▲ shows that with human gastric cancer cell line NUGC4-derived tumor tissue.

In FIG. 6, ●—● shows reactivity of ALC-390 with human normal lung tissue; o—o shows that with human pulmonary adenocarcinoma tissue; △—△ shows that with human pulmonary adenocarcinoma cell line PC-9-derived tumor tissue; and ◇—◇ shows that with human pulmonary adenocarcinoma cell line A549-derived tumor tissue.

FIGS. 7A, 7B, and 7C show the results of protein staining and immunostaining of the PVDF membrane which was subjected to the western blotting. FIG. 7A shows the results of protein staining with Coomassie brilliant blue. FIG. 7B shows the results of immunostaining using normal mouse serum. FIG. 7C shows the results of immunostaining using ALC-390. In FIG. 7, a sample applied to each lane is as follows. lane 1: ALC-390-binding Sepharose 4B gel which did not adsorb NUGC4 tissue membrane component, lane 2: molecular weight markers: phosphorylase B, M.W. 92,500;

Figure 1:
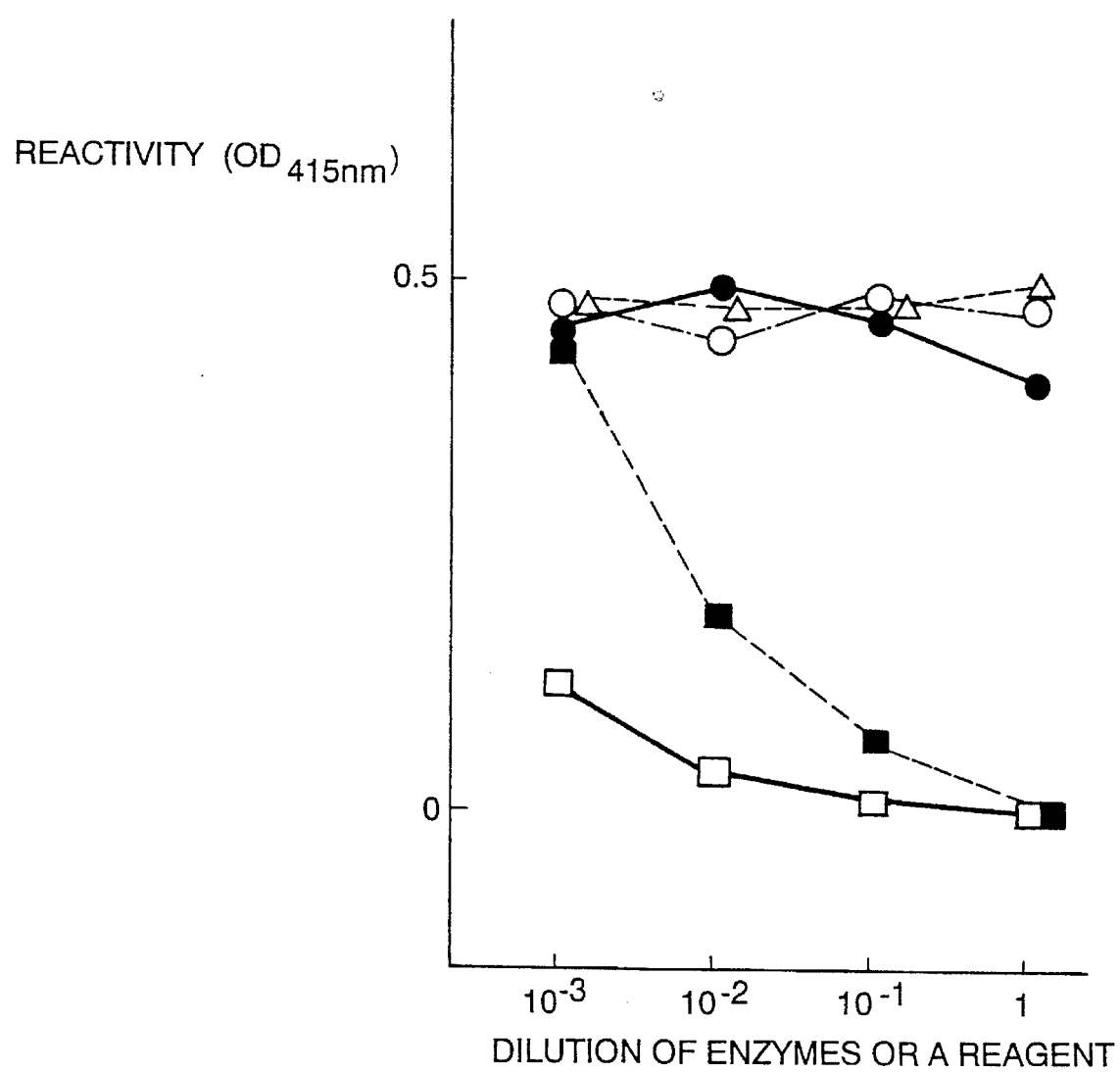
FIG. 1 shows a result of analysis of the antigen determinant recognized by the monoclonal antibody ALC-390.

bovine serum albumin, 66,200; ovalbumin, 45,000; carbonic anhydrase, 31,000; soybean trypsin inhibitor, 21,500; lysozyme, 14,000, lane 3: ALC-390-binding Sepharose 4B gel which adsorb NUGC4 tissue membrane component, lane 4: NUGC4 tissue membrane component.

DETAILED DESCRIPTION OF THE INVENTION

The present invention provides an antihuman pulmonary adenocarcinoma monoclonal antibody which is obtained by fusing mouse spleen cells immunized with a human pulmonary adenocarcinoma tissue membrane component with mouse myeloma cells to give hybridomas; selecting a monoclonal antibody reactive to a human pulmonary adenocarcinoma cell membrane; incubating the selected hybridomas in a medium or administering the same to a mouse; and then collecting the desired monoclonal antibody from the incubation medium or from the ascites fluid of the mouse.

The monoclonal antibody of the present invention belongs to the IgG class, reacts with pulmonary adenocarcinoma cell membrane and recognized this protein as an antigen.

Examples of the monoclonal antibody of the present invention include ALC-390 which is produced by a hybridoma cell strain ALC-390 deposited with European Collection of Animal Cell Culture in England on Mar. 26, 1987 as ECACC No. 87032601 under the Budapest treaty.

A process for producing the monoclonal antibody of the present invention will now be described in detail.
(1) Immunization of animal and preparation of antibody-producing cells Mice aged three to ten weeks, preferably eight weeks, are immunized with human pulmonary adenocarcinoma cells, or a tissue or membrane component thereof, to prepare antibody-producing cells in the spleen, lymph nodes and peripheral blood of each mouse. It is preferable that the mice to be immunized are preliminarily treated with human normal lung cells to make the aminals immunologically tolerant. The immunization may be effected by subcutaneously, intravenously or intraperitoneally administering $10^6$ to $10^7$ human pulmonary adenocarcinoma cells, a human pulmonary adenocarcinoma tissue or membrane components thereof (10 to 500 μg) to each animal together with an appropriate adjuvant such as complete Freund's adjuvant or aluminum hydroxide gel combined with B. pertussis vaccine. The antigen is again administered to the animal two to five times at one to two week intervals. Three to seven days after each immunization, the blood of the animal is collected from the fundus plexus venosus and the reaction of the collected serum with human pulmonary adenocarcinoma is examined by, for example, the following enzyme immunoassay method (cf. Enzyme-linked Immunosorbent Assay (ELISA), published by Igaku Shoin, 1976).
Enzyme Immunoassay 100 to 200 μl portions of membrane components of normal or tumor cells, i.e., membrane fragments, each containing 10 to 1,000 μg/ml of proteins are pipetted into a 96-well EIA plate manufactured by Flow Laboratories. After allowing the plate to stand at 4° C. for one to two days, the supernatant in each well is removed and the residue is thoroughly washed with deionized water or a phosphate buffer solution (PBS: comprising 1.83 g of disodium phosphate, 0.21 g of monopotassium phosphate, 7.65 g of sodium chloride and 1 l of distilled water, pH 7.2). Then, 100 to 200 μl of a 1 w/v % solution of bovine serum albumin (BSA) in PBS is pipetted into each well and the plate is allowed to stand at 4° C. for one to two days to thereby block the binding residues with proteins remaining on the plate. Then, the BSA/PBS is discarded and the residue is thoroughly washed with deionized water or PBS. Subsequently, 100 μl portions of samples, each used as the primary antibody and obtained by diluting mouse serum, the hybridoma incubation supernatant or crude monoclonal antibody with BSA/PBS, are pipetted into each well and the plate is allowed to stand at 4° C. overnight. After washing the plate with deionized water once followed by washing with a 2M NaCl solution six times, 100 μl of rabbit antimouse immunoglobulin/peroxidase complex (manufactured by DAKO and marketed by Kyowa-Medex) diluted 100-fold are pipetted into each well and then the plate is allowed to stand at room temperature for two hours.

After thoroughly washing the plate with PBS, the coloration is determined by the absorbance at $OD_{415nm}$ with the use of an ABTS substrate solution which is obtained by dissolving 550 mg of diammonium 2,2'-azinobis(3-ethylbenzothiazoline-6-sulfonate in 1 l of a 0.1M citrate buffer solution (pH 4.2) and adding 1 μl/ml of hydrogen peroxide thereto immediately before use. Then, a mouse showing an intense reactivity with pulmonary adenocarcinoma cells or tissue or membrane component thereof is employed as a human pulmonary adenocarcinoma immunized mouse providing antibody-producing cells in the preparation of the hybridoma.

When cells per se are to be used as an antigen, the enzyme immunoassay is carried out by incubating target cells on an Falcon 3072 plate; adding 0.25 v/v % glutaraldehyde in PBS thereto; allowing the plate to stand at room temperature for one to two hours; thoroughly washing the same with PBS; further adding 100 to 200 μl of 1 w/v % BSA in PBS; thoroughly washing the same with deionized water or PBS; and determining the antibody titer in the same manner as the use of the coat plate as obtained above.

Three to four days before cell fusion, 2 to $5 \times 10^6$ of human pulmonary adenocarcinoma cells or 20 to 400 μg of human pulmonary adenocarcinoma tissue or membrane components thereof are intraperitoneally administered to an immunized mouse. Then, the spleen of the animal is removed and minced in MEM (manufactured by Nissui Pharmaceutical Co., Ltd.). The pieces are loosened with a pincette and cetrifuged at 1,200 rpm for five minutes. After discarding the supernatant, the residue is treated with a tris/ammouium chloride buffer solution (pH 7.65) for one to two minutes to thereby remove erythrocytes. After washing with MEM three times, cells for fusion can be obtained.

The membrane component of a human pulmonary adenocarcinoma tissue is prepared in the following manner.

A tissue pieces stored at −80° C. are thawed and cut into pieces with scissors. Then, the pieces are mechanically ground with an Ultra-Disperser (manufactured by Yamato), homogenized with a glass Teflon homogenizer and then cetrifuged at 100,000×g for 20 minutes. The supernatant is further centrifuged at 4° C. and at 100,000×g for one hour and the precipitate thus obtained is suspended in a 0.01M phosphate buffer solution (pH 7.2). This suspension is employed as the membrane component.
(2) Preparation of Myeloma Cells An established cell line obtained from a mouse is employed as the source of myeloma cells. Examples of suitable myeloma cells include 8-azaguanine resistant mouse, originating from BALB/c, myeloma cell lines P3-X63Ag8-U1 (P3-U1) [cf. Current Topics in Microbiol. Immunol. 1; and Europ. J. Immunol., 6, 511–519 (1976)];

SP2/0-Ag14 (SP-2) [cf. Nature, 276, 269–270 (1978)]; P3-X63-Ag8653 (653) [cf. J. Immunol., 123, 1548–1550 (1979)]; and P3-X63-Ag8 (X63) [cf. Nature, 256, 495–497 (1975)]. These cell lines are subcultured in an 8-azaguanine medium which is obtained by adding 1.5 mM of glutamine, $5 \times 10^{-5}$M of 2-mercaptoethanol, 10 µg/ml of gentamycin and 10 v/v % of fetal calf serum to an RPMI-1640 medium to give a medium, which will be called the "normal medium" hereinafter, and further adding 15 µg/ml of azaguanine thereto. These cell lines are subcultured into the normal medium three or four days before the cell fusion to thereby secure a cell count of at least $2 \times 10^7$ on the day of the cell fusion.

(3) Cell Fusion

The antibody-producing cells as immunized in (1) and the myeloma cells as obtained in (2) are thoroughly washed with the MEM medium or PBS. Then, these cells are mixed together in such a manner as to give a cell count ratio of the former to the latter of 5 to 10:1. The resulting mixture is centrifuged at 1,200 rpm for five minutes and then the supernatant is discarded. The precipitated cells are thoroughly loosened and 0.2 to 1 ml/$10^3$ antibody-producing cells of a mixture comprising 2 g of polyethylene glycol 1,000 (PEG-1,000), 2 ml of MEM and 0.7 ml of dimethyl sulfoxide are added thereto at 37° C. under stirring. Then, 1 to 2 ml portions of MEM are further added therero several times at one to two minute intervals to thereby adjust the total volume of the mixture to 50 ml. After centrifuging the mixture at 900 rpm for five minutes, the supernatant is discarded and the cells are slowly loosened. 100 ml of the normal medium RPMI-1640 containing 10 v/v % of FCS is added thereto and the cells are slowly suspended in the medium by inhaling and blowing through a volumetric pipet.

1 ml of the resulting suspension is pipetted into each well of a 24-well incubation plate and incubated in an incubator under 5% of $CO_2$ at 37° C. for 24 hours. Then, 1 ml of an HAT medium, which is obtained by adding $10^{-4}$M of hipoxanthine, $1.5 \times 10^{-5}$M of thymidine and $4 \times 10^{-7}$M of aminopterin to the normal medium, is added to each well and the plate is then incubated for an additional 24 hours. 1 ml of the incubation supernatant in each well is discarded and the same amount of fresh HAT medium is added at 24 hour intervals for the following two days. The incubation is continued in a $CO_2$ incubator at 37° C. for 10 to 14 days.

In a well where fused cells form colonies, 1 ml of the supernatant is discarded and the same amount of an HT medium obtained by removing aminopterin from the HAT medium is added. The conversion into the HT medium is carried out at 24 hour intervals for the following two days.

After incubating the cells in the HT medium for three to four days, some portion of the incubation supernatant is collected and the antibody titer thereof against human pulmonary adenocarcinoma is determined according to the above-mentioned enzyme immunoassay. Then, the reactivity of the incubated cells with human normal cells, tissue and membrane components thereof are determined in the same manner. Thus, wells specifically reacting with human pulmonary adenocarcinoma cells or tissue or membrane components thereof are selected. Wells which do not react with human normal cells, tissue or membrane components thereof but which intensely react with human pulmonary adenocarcinoma cells or tissue or membrane components thereof are subjected to cloning twice by limiting dilution analysis to thereby select a cell line which shows a stable antibody titer against human pulmonary adenocarcinoma cells or tissue or membrane components thereof as an antihuman pulmonary adenocarcinoma monoclonal antibody-producing hybridoma line.

(4) Preparation of Monoclonal Antibody 2 to $4 \times 10^6$ antihuman pulmonary adenocarcinoma monoclonal antibody-producing hybridoma cells as obtained in (3) are intraperitoneally injected into a female nude mouse aged eight to ten weeks which has been treated with pristane by intraperitoneally administering 0.5 ml of 2,6,10,14-tetramethylpentadecane (pristane) followed by feeding for two weeks. After 10 to 21 days, the hybridoma cells become ascites cancer cells. The ascites fluid is collected from the mouse and centrifuged at 3,000 rpm for five minutes. After removing solid matter, the residue is salted-out with 50% saturated ammonium sulfate, dialyzed against a 0.04M phosphate buffer solution (pH 8.0, containing 0.03M of NaCl) and passed through a DE52 column (manufactured by Whatman). IgG fractions are collected to thereby give the desired monoclonal antibody in a purified state.

The isotype of the antibody is determined by Ouchterlony's method (double immunodiffusion) (cf. Menekigaku Numon, Seibutsu Kagaku Jikkenho 15, Gakkai Shuppan Center, p. 74 (1981)).

Protein is determined by Folin's reaction and the absorbance at 280 nm [1.4 ($OD_{280}$)=1 mg/ml of immunoglobulin].

The specificity of the monoclonal antibody thus obtained is determined by, for example, evaluating the reactivities with normal or tumor tissues or membrane components thereof originating from various human organs obtained from two or more samples; those with various human normal or tumor cell strains or fetal human cell strains or membrane components thereof; or those with known carcinoembryonic antigens such as CEA by enzyme immunoassay or immunohistrological (PAP) methods. In any case, monoclonal antibody which scarcely reacts with antigens other than human pulmonary adenocarcinoma should be selected.

(5) Analysis of Antigen

Upon the above-mentioned enzyme immunoassay or immunohistological staining, an antigen selected from pulmonary adenocarcinoma membrane components, pulmonary adenocarcinoma cell strains and pulmonary adenocarcinoma tissues is pretreated with an enzyme such as neuraminidase or protease or a reagent such as periodic acid and then reacted with the monoclonal antibody. Thus, the chemical properties of the antigen, i.e., the chemical properties of the antigen site recognized by the monoclonal antibody, are determined from the difference between the reactivity of the treated antigen, as described above, and that of the untreated antigen each with the monoclonal antibody. That is to say, it is assumed that sialic acid, protein or a sugar chain might relate to the antigen determinant when the antigenecity is lost by treating with neuraminidase, protease or periodic acid, respectively.

Western blot analysis is performed to define the molecular weight of the antigen. Two pulmonary adenocarcinoma-membrane fractions and two normal lung membrane fractions are separated by SDS-PAGE, transferred to PVDF (polyvinylidene difluoride membrane; Clear Blot Membrane-P; Atto), and immunostained with ALC-390.

In order to investigate the antigen recognized by ALC-390 in more detail, the antigen was purified and analyzed for its structure.

(6) Scatchard Analysis

Direct binding assay of $^{125}$I-labeled ALC-390 against a colon carcinoma cell line SW1116 (ATCC CCL233) is carried out and the result is analyzed by the method of Scatchard [Immunological Methods, 2, 1–26 (1981)].

(7) In Vivo Localization of ALC-390

In vivo localization of ALC-390 is examined by injecting $^{125}$I-labeled ALC-390 into mice bearing SW1116 tumors.

(8) Ditection of Serum Antigen

To investigate whether the antigen recognized by ALC-390 is shed from the cancer cells or not, the antigen level in sera from 23 healthy adults and 16 patients with pulmonary adenocarcinoma is examined by sandwich-type ELISA and inhibition ELISA. Detectable level of the antigen recognized by ALC-390 is not found in any sera examined.

To further illustrate the present invention, the following Examples will be given but is no way intended to limit the scope of the present invention.

EXAMPLE 1

(1) Preparation of Antibody-producing Cells

Normal human lung membrane components (100 μg/animal on a protein basis) were intravenously administered to newborn BALB/c mice (obtained from Shizuoka Jikken Dobutsu) within 24 hours after birth. Eight weeks later, 100 μg on a protein basis of a human pulmonary adenocarcinoma membrane fragment was intraperitoneally administered to each mouse together with 2 mg of aluminum hydroxide gel and $1\times10^9$ of dead *B. pertussis* vaccine cells. Subsequently the animal was immunized with 100 μg portions on a protein basis of the same antigen three to five times at one to two week intervals. Among these mice, those showing antisera highly reactive with human pulmonary adenocarcinoma cells or tissue or membrane components thereof were referred to immunized mice and spleen cells obtained therefrom were subjected to cell fusion.

(2) Preparation of Mouse Myeloma Cells

An 8-azaguanine resistant mouse myeloma cell line P3-U1 was incubated in the normal medium to give $2\times10^7$ or more cells which were used as parent cells at the cell fusion.

(3) Prepareation of Hybridomas

The spleen cells and myeloma cells obtained in (1) and (2), respectively, were fused in the above-mentioned manner in a ratio of 5:1 and incubated in HAT medium at 37° C. for 14 days under 5% of $CO_2$. Then, fused cells were selected and further incubated in an HT medium. The antibody titer against antihuman pulmonary adenocarcinoma of each well was determined and active wells were transplanted into a normal medium. After repeating cloning twice, a hybridoma cell line ALC-390 producing a monoclonal antibody, which would never react with normal human cells or tissues but would react with human pulmonary adenocarcinoma, was selected through an enzyme immunoassay method, an immunohistochemical staining method and an immunocytochemical staining method.

(4) Purification of Monoclonal Antibody $4\times10^6$ of the hybridoma cells ALC-390 as obtained (3) were intraperitoneally injected to female nude mice aged eight weeks which had been treated with pristane. 10 to 21 days thereafter, the hybridomas became ascites cancer cells. 5 to 10 ml portions of the ascites fluids were collected from the animals showing standing ascites fluids. These acsites fluids were combined and centrifuged at 3,000 rpm for five minutes. After removing solid matter, the residue was salted out with 40% saturated ammonium sulfate and dialyzed against a 0.04M phosphate buffer solution (pH 8.0, containing 0.03M of NaCl). Then, it was passed through a DE52 column (manufactured by Whatman, bed volume: 50 ml) at a flow rate of 20 to 30 ml/hr. IgG fractions were collected to obtain the purified monoclonal antibody.

(5) Specificity of ALC-390

Table 1 shows the reaction specificities of the antihuman pulmonary adenocarcinoma monoclonal antibody ALC-390 thus obtained.

The determination was carried out by ELISA in the following manner.

Utilization of Tissue (Membrane Component) as Target

50 μl of a 0.1 mg/ml soluiton of the target tissue (membrane component) were pipetted into each well of a 96-well ELISA plate (manufactured by Linbro). The plate was allowed to stand at 37° C. for two hours or at 4° C. overnight to thereby fix the tissue (membrane component). After washing the plate with PBS, 100 μl of PBS containing 10 v/v % of FCS was pipetted into each well to thereby protect the active residues of the fixed tissue (membrane component). After washihg with PBS. 50 μl of the primary antibody (ALC-390) was added to each well and the plate was allowd to stand at 37° C. for one to two hours or at 4° C. overnight, thus reacting the target with the antibody. Then, the plate was washed with PBS containing 0.05 v/v % of Tween-20 (manufactured by Wako Pure Chemical Industries Co.) five times to remove the unreacted antibody. 50 μl of the secondary antibody, which was rabbit antimouse immunoglobulin binding to peroxdiase (manufactured by Miles-Yeda, diluted 200-fold), was added to each well and allowed to react at 37° C. for one hour. The plate was washed with PBS containing 0.05 v/v % of Tween-20 five times and then with deionized water three times.

50 μl of ABTS was added to each well to thereby initiate the reaction and 50 μl of a 5 w/v % aqueous solution of sodium lauryl sulfate was added to terminate the reaction.

Utilization of Cultured Cells as Target

The target cells were incubated in a 96-well incubation plate (manufactured by Linbro). When the cells became confluent, the same reactions as those described above with respect to the case of target tissue (membrane component) were carried out except both of the primary and secondary antibodies were reacted at room temperature for 30 minutes. The reaction mixture was transported into a 96-well analysis plate after coloration to terminate the reaction.

When an antigen CEA was employed as the target, the above procedure was followed except that the tissue (membrane component) was replaced with CEA. In each case, the absorbance of the reaction mixture was determined at 415 nm while using that at 490 nm as a control.

TABLE 1-1

| Antigen | Reactivity (ELISA) positive sample/ total sample |
| --- | --- |
| Tissue membrane component | |
| pulmonary adenocarcinoma | 7/10[a] |
| lung squamous cell carcinoma | 1/12 |
| normal lung | 0/6 |
| other normal tissues[b] | 0/11 |
| Cultured cell line | |
| lung cancer[c] | 3/8 |
| pancreatic cancer | 1/1 |
| colon cancer | 2/2 |
| stomach cancer | 3/3 |
| other cancers[d] | 3/5 |
| Antigen | |
| CEA | 0/1 |

Note:
[a]: Number of positive samples/Total number of samples.
[b]: Liver, kindney, stomach, pancreas, intestine, spleen, heart, medulla, lymphocyte, erythrocyte and brain.
[c]: Pulmonary adenocardinoma: 2/3
[d]: Uterine cancer, prostate cancer and melanoma.

As shown in Table 1-1, ALC-390 was highly specific to pulmonary adenocarcinoma cells but did not react with CEA. These facts suggest that it is different from antiCEA antibody.

Further, the reactivity of ALC-390 with various cell lines was examined by the immunocytochemical staining and immunofluorescence assay.

Immunocytochemical Staining

Cell suspensions in culture medium were incubated at 37° C. for overnight and attached on 12 well multitest slide (Flow Laboratories, Irvine, U.K.). Adherent cells were washed with PBS, fixed with acetone for 5 minutes at −20° C., and airdried. Then endogenous peroxidase was blocked and fixed cells were immunostained using a Vestastain ABC kit (Vector Laboratories) according to the recommended procedure described in the text of Vector Laboratories. Briefly, after treatment with normal horse serum, culture supernatants of hybridoma or purified ALC-390 were incubated on the slide for 30 minutes and rinsed off with PBS. Biotinylated anti-mouse immunoglobulin horse antibody was incubated on the slide for 30 minutes and washed with PBS. Then, avidin-biotinylated horseradish peroxidase was incubated for 1 to 5 minutes in peroxidase substrate solution (mixture of 0.02% hydrogen peroxide and 0.1% diaminobenzidine tetrahydrochloride in 0.1M Tris buffer, pH 7.2). After washing with distilled water, the slide was counterstained with hematoxylin, dehydrated in ethanol, washed in xylene, and mounted.

$1 \times 10^5$ cells and the reaction mixture was incubated for 30 minutes on ice. After washing 3 times with PBS, 20 μl of fluorescence isothiocyanate-conjugated rabbit anti-mouse immunoglobulin (Miles-yeda, Rehovot, Israel) were allowed to react for 30 minutes on ice. Fluorescence was visualized by incident illumination using a Nikon fluorescence microscope.

Furthermore, the reactivity of ALC-390 with red blood cells was examined by the following hemagglutination assay.

Hemagglutination Assay

Culture supernatant was tested for hemagglutinating activity by mixing 50 μl of 1% (v/v) suspension of human erythrocytes in PBS in each well of a 96-well U-plate. After incubating at room temperature for 1 hour, wells were examined microscopically for direct hemagglutination.

The reactivity with various cell lines and red blood cells examined by the above immunocytochemical staining, immunofluorescence assay and hemagglutination assay is illustrated in Table 1-2.

TABLE 1-2

| Assay | Cell | Reactivity Positive | Negative |
|---|---|---|---|
| Immunocyto-chemical staining | Lung Cancer | | |
| | Adenocarcinoma | A549*, HCL-1*, RERF-LC-MS, Darby, PC-9 | PC-12* |
| | Squamous cell carcinoma | SK-LC-4 | PC-1*, PC-10*, Calu-1* |
| | Large cell carcinoma | PC-13*, Calu-6 | SK-LC-6 |
| | Small cell carcinoma | QG90 | PC-6* |
| | Stomach cancer | MKN-1*, MKN-28*, MKN-45* | — |
| | Colon cancer | Colo205*, SW1116* | — |
| | Pancreatic cancer | HPAF*, CAPAN-1, CAPAN-2 | — |
| | Mammary cancer | MCF-7, R-27, HBC-7, 5C, 4W, T47D | — |
| | Uterine cancer | Hela*, RL95-2* | — |
| | Chorio cancer | Enami | — |
| | Prostate cancer | PC-3* | — |
| | Melanoma | — | SK-26*, SK-28* |
| | Normal | — | CCD-13Lu, CCD-8Lu (Lung), YH-1, YH-3 (Fibroblast) |
| | Fetal | L132 (Lung), Flow7000 (Skin) | IMR90 (Lung), DETROIT-551 (Skin) |
| Immunofluorescence assay | Lung adenocarcinoma | PC-7 | — |
| | Stomach cancer | Kato3 | — |
| | Leukemia | K562 | Molt-3, HSB-2, NALL-1, Raji, NALM-6, HL-60 |
| | Myeloma | — | Sk-Ly-18 |
| Hemmagglutination assay | Erythrocyte | — | A1-, A2-, B-, 0-Type |

Note:
Cell lines bearing asterish are the antigens used in ELISA of Table 1-1.

Immunofluorescence Assay

Target cells from cell line culture were washed 3 times with PBS and resuspended at $2 \times 10^6$ cells/ml in PBS. Fifty μl of a sample were added to each Eppendorf tube containing As shown in Table 1-2, ALC-390 reacted well with tumor cell lines of adenocarcinoma including lung cancer, stomach cancer, colon cancer, mammary cancer and uterine cancer. Two of 4 fetal cell lines were reacted with ALC-390.

However, ALC-390 did not react with almost any examined cell lines of melanoma, leukemia, myeloma and normal tissues. ALC-390 did not agglutinate any $A_1$, $A_2$, B or O blood-group erythrocyte.

(6) Classification of the Isotype of ALC-390

The isotype of antihuman pulmonary adenocarcinoma monoclonal antibody ALC-390 was determined by Ouchterlony's method. As a reuslt, it is found that the antibody ALC-390 belongs to IgG class, more specifically, $IgG_1$ class.

EXAMPLE 2

Sections of various normal adult and fetal organs and cancer tissues, which were fixed with formalin, embedded in paraffin and sliced with a microtome at a thickness of 5 μm, were each fixed on a glass slide coated with egg white albumin. After removing the paraffin with xylene, each section was made hydrophilic stepwise using alcohol-water. Then, each section was rinsed with deionized water for five minutes and allowed to stand in methanol containing 0.3% of $H_2O_2$ at room temperature for 30 minutes to block endogenous peroxidase. Then, the section was washed with PBS for 20 minutes and allowed to stand in diluted normal equine serum at room temperature for 20 minutes. After removing the excessive serum, the section was reacted with the primary antibody (antihuman pulmonary adenocarcinoma monoclonal antibody ALC-390, 10 μg/ml) for 30 minutes. After washing, the reaction mixture was reacted with a diluted biotinized antibody (biotinized rabbit antiIgG antibody) for 30 minutes. After washing, it was further reacted with an avidin/biotin/peroxidase complex (manufactured by Vector) for 30 minutes. Then, the reaction mixture was thoroughly washed and reacted with a peroxidase substrate, which was a 0.1% solution of diaminobenzidine tetrahydrochloride in a 0.1M tris hydrochloride butter solution (pH 7.2) containing 0.02% of $H_2O_2$, for two minutes; the reaction was stopped by ice-cooling. After staining with hematoxylin and dehydrating with an aqueous alcohol and xylene solution, the residue was fixed with Canada balsam and observed under a microscope.

The results are shown in Table 2.

TABLE 2

| Carcinoma | No. of samples | Reactivity* ++ | + | ± | − |
|---|---|---|---|---|---|
| Pulmonary adeno | 9 | 7 | 0 | 0 | 2 |
| Lung squamous cell | 11 | 0 | 1 | 1 | 9 |
| Lung small cell | 7 | 0 | 0 | 0 | 7 |
| Lung large cell | 6 | 1 | 1 | 1 | 3 |
| Gastric | 5 | 0 | 1 | 1 | 3 |
| Colorectal | 6 | 1 | 2 | 0 | 3 |
| Pancreatic | 3 | 1 | 1 | 0 | 1 |
| Hepatic | 5 | 0 | 0 | 1 | 4 |
| Mammary | 8 | 4 | 2 | 2 | 0 |
| Ovary | 4 | 1 | 2 | 0 | 1 |
| Cervical | 4 | 0 | 1 | 1 | 2 |

Note:
*++, more than 40% of tumor cells were positive; +, 10 to 40% of tumor cells were positive; ±, 1 to 10% of tumor cells were positive; −, no tumor cells were positive.

As shown in Table 2, ALC-390 slightly reacted with lung squamous cell carcinoma and some cells of a lung large cell carcinoma tissue but reacted intensely with pulmonary adenocarcinoma at a high ratio. In addition to pulmonary carcinoma tissues, positively stained tumor cells were observed in 21 of 35 specimens. Especially, all mammary carcinomas tested were reacted with ALC-390. As a result of this test, the immunoreaction of ALC-390 occurred at the cell membrane. A positive finding was observed in a small number of cells in normal tissues like lung, intestine, pancreas, liver and kidney (as shown in Table 3). Tissues from neonates and a fetus (39 weeks) were tested and almost the same findings were observed as those seen with the adult tissues (as shown in Table 4).

TABLE 3

| Tissues | Positive findings |
|---|---|
| Lung | Bronchial epithelium (7/17), bronchial glands (1/1), proliferating type II cells (10/17) |
| Stomach | Negative (0/1) |
| Small intestine | Epithelium of intestinal glands (2/3) |
| Large intestine | Epithelium of intestinal glands (2/2) |
| Pancreas | Epithelium of pancreatic duct (3/3), acinar cells (3/3) |
| Liver | Epithelium of gallbladder duct (4/5) |
| Kidney | Convulted tubule (4/5)* |
| Spleen | Negative (0/3) |
| Thyroid | Negative (0/3) |
| Heart | Negative (0/3) |
| Bone marrow | Negative (0/1) |
| Brain | Negative (0/2) |
| Spinal cord | Negative (0/1) |

Note:
*Stained partly

TABLE 4

| Tissues | Positive findings |
|---|---|
| Lung | Bronchial epithelium (3/3) |
| Esophagus | Negative (0/1) |
| Stomach | Negative (0/1) |
| Small intestine | Goblet cells (2/2)* |
| Large intestine | Intestinal glands (2/2), Superficial epithelium (2/2) |
| Liver | Epithelium of gallbladder duct (2/2) |
| Kidney | Convulted tubule (3/3)* |
| Adrenal gland | Negative (0/2) |
| Bone marrow | Negative (0/1) |
| Skin | Sebaceous gland (3/3) |
| Brain | Negative (0/1) |

Note:
*Stained partly

EXAMPLE 3

The antigen determinant recognized by the monoclonal antibody ALC-390 was analyzed by reacting ALC-390 with pulmonary adenocarcinoma membrane components which was each treated with the following enzymes and reagents prior to the reaction.

Enzymes and Reagents

Trypsin (GIBCO, 2.5 w/v % solution): dissolved in PBS to give a final concentration of 0.25 w/v %.

Neuraminidase (Boehringer Mannheim): dissolved in 0.1M acetate buffer (pH 4.5) containing 3 mM $CaCl_2$ to give a final concentration of 0.1 U/ml.

α-L-Fucosidase (Boehringer Mannheim): dissolved in 0.1M phosphate buffer (pH 6.3) to give a final concentration of 0.1 U/ml.

Protease (Sigma): dissolved in 0.1M phosphate buffer (pH 7.2) to give a final concentration of 10 U/ml.

$NaIO_4$ (Wako Pure Chemical): dissolved in PBS to give a final concentration of 50 mM.

Pulmonary adenocarcinoma membrane components (100 μg protein/ml) was dispensed in 50 μl portions into each well of an EIA plate (Linbro). After allowing the plate to stand overnight at 4° C., each well was washed with PBS three times. Then, 200 µl of 1 w/v % BSA-PBS was pipetted into each well and the plate was allowed to stand at room temperature for 0.5 to 2 hours. After washing each well with PBS three times, the above-described enzyme solution or reagent solution was each dispensed in 50 µl portions into each well and allowed to react at 37° C. for an hour. Then, each well was washed with PBS five times and 50 µl of the monoclonal antibody ALC-390 (10 µg/ml) was pipetted into each well, followed by allowing the plate to stand overnight at 4° C.

Then, each well was washed with Tween 20-PBS (Tween 20: Wako Pure Chemical) five times and 50 µl of peroxidase-labeled mouse IgG (400-fold dilution) was pipetted into each well. After reaction at room temperature for 2 hours, each well was washed with Tween 20-PBS five times. ABTS substrate solution was dispensed in 100 µl portions into each well and allowed to react at room temperature for 30 minutes, and thereafter the absorbance of the reaction mixture in each well was measured at 415 nm.

As shown in FIG. 1, the antigenecity was lost by treatment with trypsin and protease. Therefore, it is assumed that the monoclonal antibody ALC-390 recognizes protein as the antigen determinant.

EXAMPLE 4

Proteins derived from membrane fractions were separated by SDS-PAGE on a vertical slab gel apparatus (Atto Corporation, Tokyo, Japan) as originally described by Laemmli [Nature, 227, 680 (1970)] using 5–20% polyacrylamide gradient gel. After electrophoresis, the proteins from the polyacrylamide gel were transferred to PVDF membrane (Clear Blot Membrane-P; Atto) at 2 mA/cm$^2$ for using an Atto transblot apparatus in a transbuffer containing 0.1M Tris; 0.192M glycine: 20% (v/v) methanol. For the detection of transferred protein, the membrane was stained with Coomassie brilliant blue. For the immunostaining by ALC-390, the membrane was incubated for 1 hour in a blocking buffer consisting of 1% BSA-PBS followed by over night incubation at 4° C. with ALC-390 (10 µg/ml in 1% BSA-PBS) or normal mouse serum (diluted 1000-fold in 1% BSA-PBS). After washing with 0.05% Tween-PBS, the membrane was incubated for 2 hours at room temperature with biotinylated rabbit anti-mouse immunoglobulin (Vector). After washing, the membrane was incubated for 1 hour at room temperature with avidin-peroxidase (Vector). After washing, the peroxidase activity was demonstrated using 4-chloro-1-naphthol (Bio-Rad, Richmond, Calif.) as a substrate.

Figure 2:
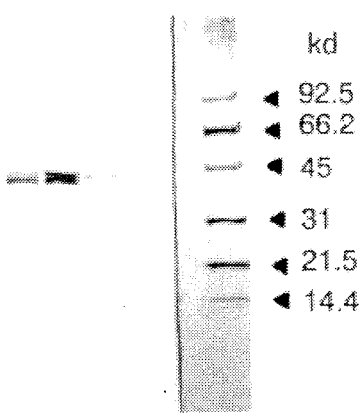
FIG. 2. shows western blot analysis of membrane fractions from pulmonary adenocarcinoma tissues and normal lung tissues. Membrane fractions (15 μg of protein) were run on SDS-PAGE (5–20% polyacrylamide gradient gel) under reducing conditions, transferred to PVDF membrane, and immunostained with normal mouse serum (lanes 1–4) and ALC-390 (lanes 5–8). Each lane shows the protein bands for the following samples. lanes 1 and 5: pulmonary adenocarcinoma tissue 1, lanes 2 and 6: pulmonary adenocarcinoma tissue 2, lanes 3 and 7: normal lung tissue 1, lanes 4 and 8: normal lung tissue 2, lane 9: molecular weight markers (Bio-Rad): phosphorylase B, M.W. 92,500; bovine serum albumin, 66,200; ovalbumin, 45,000; carbonic anhydrase, 31,000; soybean trypsin inhibitor, 21,500; lysozyme, 14,000. Molecular weight markers transferred to the membrane was detected by Coomassie brilliant blue.

In the presence of reducing agent (+2-mercaptoethanol) two immunoreactive bands were detected clearly in two pulmonary adenocarcinoma membrane fractions at an approximate M.W. 40,000 which were detected weakly in two normal lung membrane fractions (FIG. 2). Western blots were repeated both with and without the reducing agent. There were no significant difference between these two conditions.

EXAMPLE 5

(1) $^{125}$I-labeling of ALC-390

$^{125}$I-labeling of ALC-390 was performed using N-succinimidyl 3-(4-hydroxy, 3-[$^{125}$I]iodo-phenyl) propionate (mono [$^{125}$I]BHR: NEN, Boston, Mass.) described by Bolton et al. [J. Endocrinol., 55, 327 (1972)]. Three hundred µl of purified ALC-390 (1.6 mg/ml in PBS) and 100 µl of 0.2M borate buffer (pH 8.5) were added to the dried mono [$^{125}$I]BHR and the reaction mixture agitated for 5 minutes at 0° C. Then, 100 µl of 1M glycine in 0.2M borate buffer (pH 8.5) was added to the solution to stop the reaction. Free iodinate was removed by gel filtration using a G-25 Sephadex (Pharmacia Fine Chemicals, Inc.) column equilibrated with PBS. The specific activity of $^{125}$I-labeled ALC-390 were 0.6 to 2 µCi/µg.

(2) Scatchard Analysis

SW1116 cells were allowed to react with various dilutions of $^{125}$I-labeled ALC-390 with or without a large excess of ALC-390 for 90 minutes at 4° C. SW1116 cells were then washed with PBS and cell-bound radioactivity was determined. Specific binding of $^{125}$I-labeled ALC-390 was determined from the formula: specific binding=total binding (without cold ALC-390)–nonspecific binding (with cold ALC-390). Binding of $^{125}$I-labeled ALC-390 to SW1116 cells was analyzed by the method of Scatchard.

Figure 3:
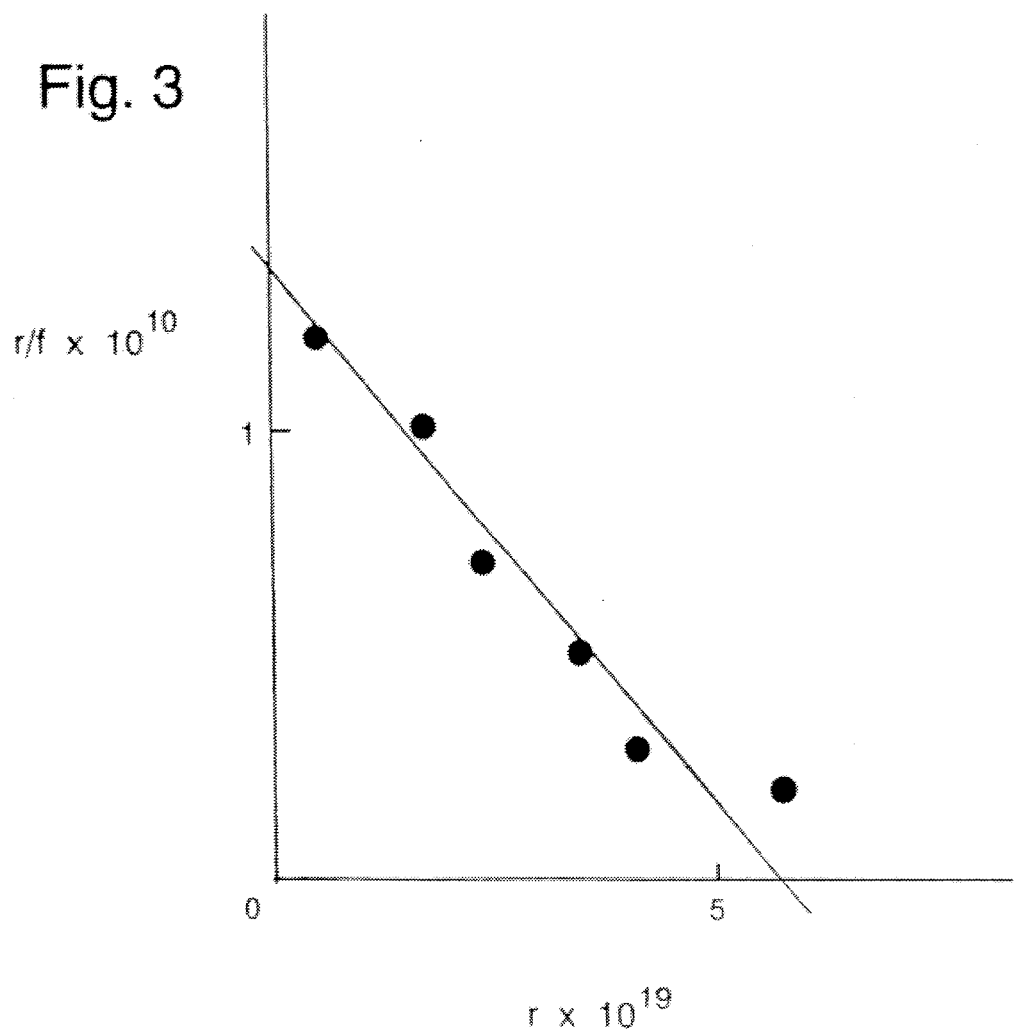
FIG. 3 shows determination of the number of ALC-390 binding sites on SW1116 cells and of the respective association constant of ALC-390. Cells were incubated with a range of concentrations of $^{125}$I-labeled ALC-390 and cell-bound radioactivity was counted: r(mol/cell) represents number of $^{125}$I-labeled ALC-390 molecule bound to each cell. f(mol/l) represents concentration of free $^{125}$I-labeled ALC-390. From the intercepts on the X-axis, the number of antigenic sites, n, was determined as approximately 3.4× $10^5$/cell. From the value of the slope, the association constant, Ka, was determined as approximately 2.3×10$^8$ liter/mol.

$^{125}$I-labeled ALC-390 was bound to SW1116 cell specifically. From the scatchard analysis, the number of ALC-390 molecules bound on per SW1116 cell was calculated approximately $3.4 \times 10^5$ cells and the association constant was $2.3 \times 10^8$ liter/mol (FIG. 3).

EXAMPLE 6

In vivo localization of ALC-390 was examined by the following procedure.

Balb/c nu/nu female, 5- to 9-week old mice (CLEA Co., Tokyo, Japan) were inoculated SW1116 tumor ($5 \times 10^6$ cells) into the subcutaneous space in the axillary region. Ten µCi of $^{125}$I-labeled ALC-390 or $^{125}$I-labeled KM-519 which is a monoclonal antibody specific for mytomycin C was injected via the tailvein into the nude mice bearing tumors of about 0.5 cm in diameter. The mice were sacrificed at 3 days and 5 days after injection. Tumor, blood, brain, heart, lung, liver, kidney, spleen, stomach, intestine, muscle, bone marrow and skin were weighed on analytical balance and assayed for radioactivity. Tissue/blood ratio was determined as follows: T/B ratio=tissue (cpm/g)/blood (cpm/g).

Figure 4A:
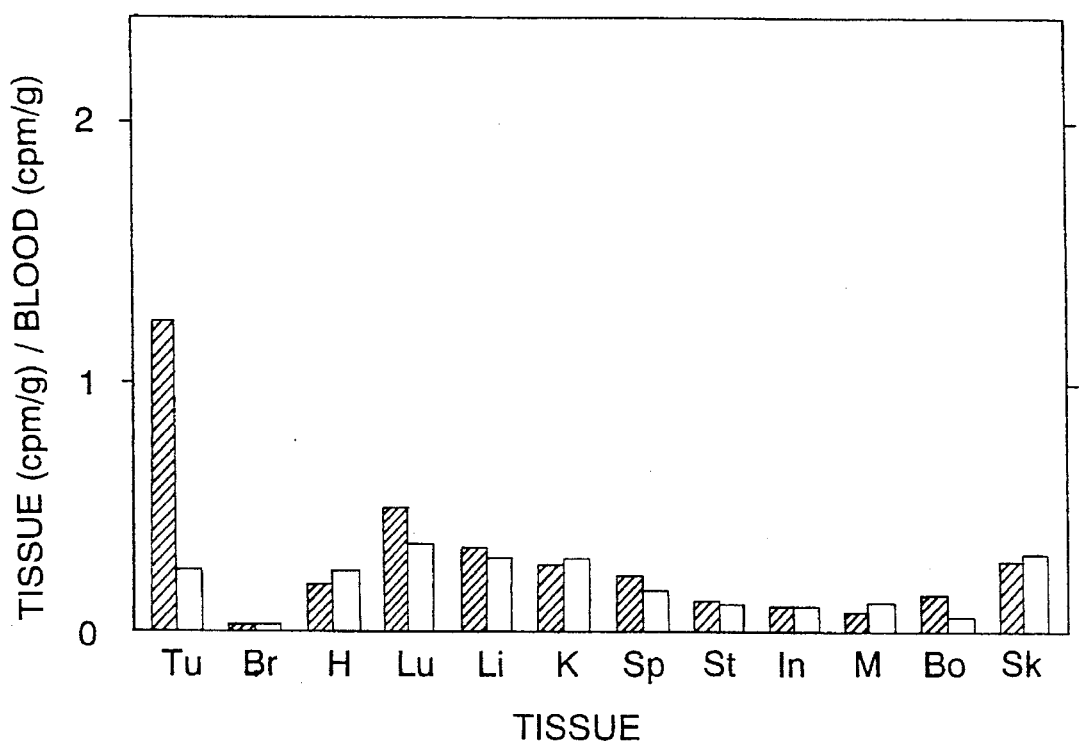
FIGS. 4A and 4B show tissue to blood ratios for monoclonal antibody ALC-390 (■) and control KM-519 (□) at 3 and 5 days after i.v. injection of 10 μCi $^{125}$I-labeled ALC-390 into nude mice bearing SW1116 xenografts. Each symbol has the following meaning. A, Day 3; B, Day 5; Tu, tumor; Br, brain; H, heart; Lu, lung; Li, liver; K, kidney; Sp, spleen; St, stomach; In, intestine; M, muscle; Bo, bone marrow; Sk, skin.
Figure 4B:
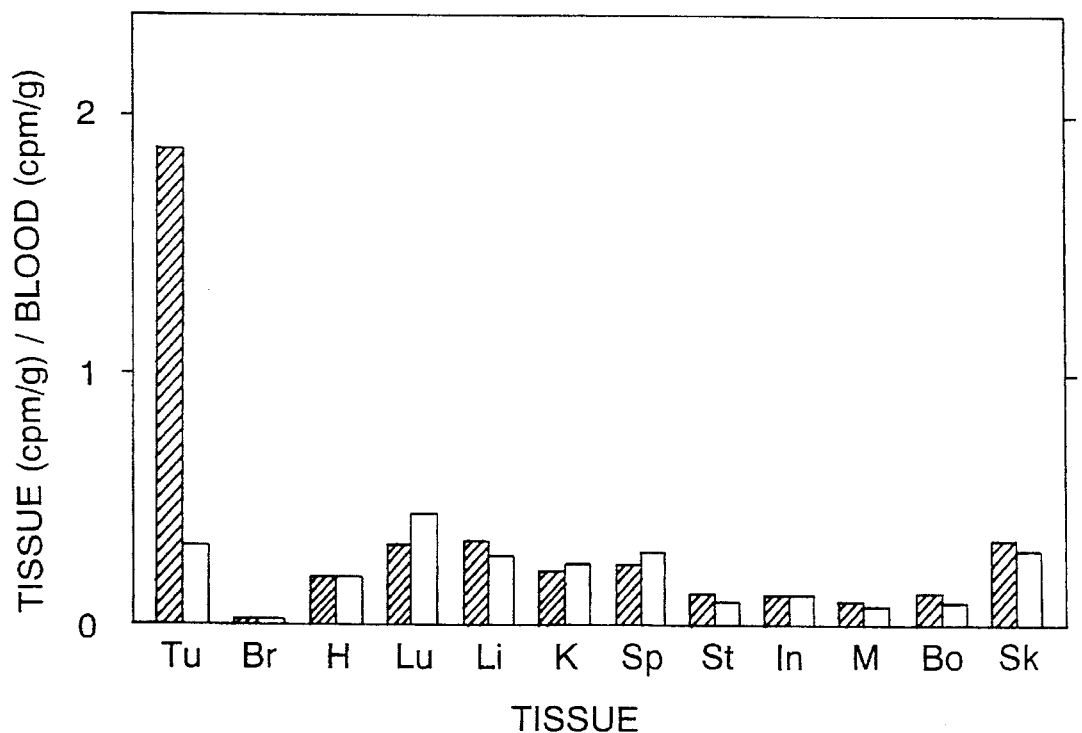

The result of in vivo localization studies of $^{125}$I-labeled ALC-390 and control monoclonal antibody KM-519 are shown in FIGS. 4A and 4B. $^{125}$I-labeled ALC-390 showed selective tumor localization following i.v. injection into nude mice bearing SW1116 xenografts at days 3 and 5 whereas no selective localization of the control monoclonal antibody was observed. The tumor to blood ratios for $^{125}$I-labeled ALC-390 were 1.21 and 1.87 at days 3 and 5, respectively.

EXAMPLE 7

(1) Preparation of human tumor tissue membrane component containing the antigen recognized by ALC-390

Human pulmonary adenocarcinoma cell line PC-9 [available from Immunobiological Laboratories (IBL)], human pulmonary adenocarcinoma cell line A549 (ATCC CCL 185) and human gastric cancer cell line NUGC4 [Japanese Journal of Cancer Research, 77, 1114 (1986)] were subcutaneously administered to nude mice and transplanted cells were allowed to fix to obtain tumor tissues. Then, reactivities of ALC-390 to the thus-obtained three tumor tissue membrane components, human pulmonary adenocarcinoma tissue membrane component and human normal pulmonary tissue membrane component were examined by enzyme immunoassay. The results are shown in FIG. 5 and FIG. 6.

Figure 5:
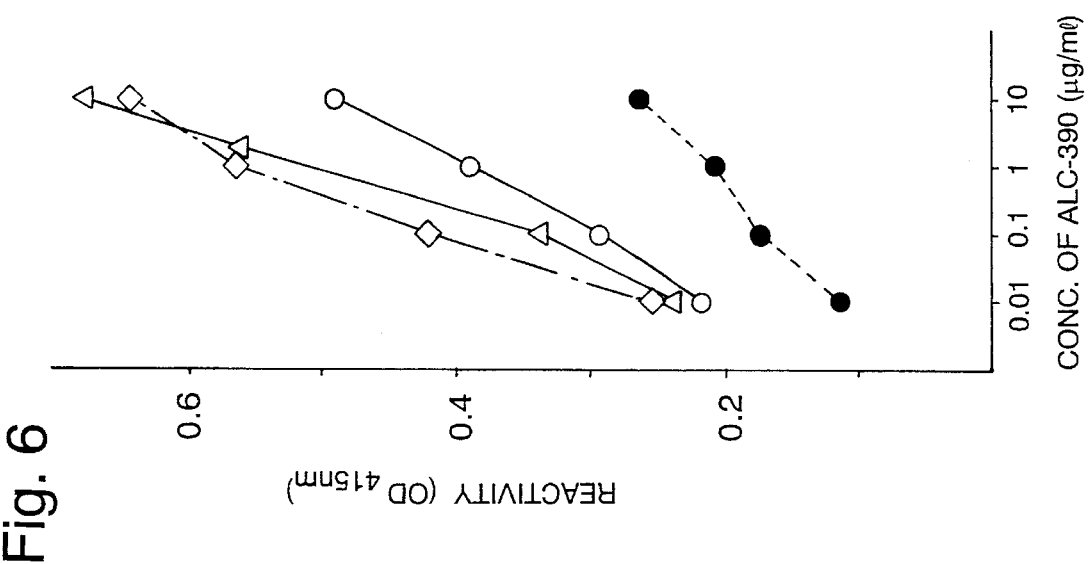
FIG. 5 shows reactivities of ALC-390 with various human tissue membrane components.
Figure 6:
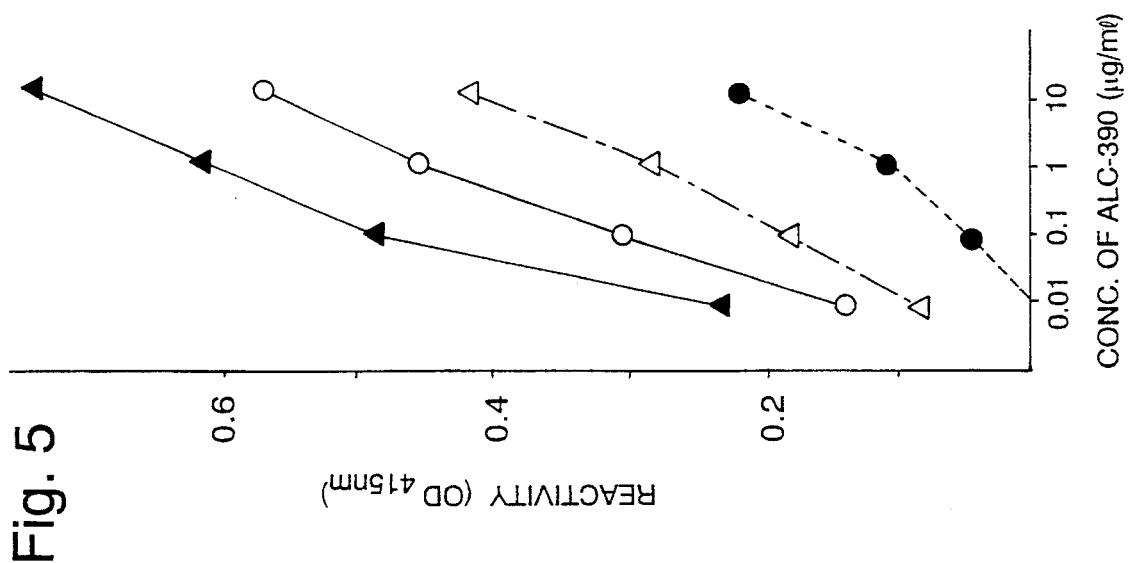
FIG. 6 shows reactivities of ALC-390 with various human tissue membrane components.

It is apparent from FIG. 5 and FIG. 6 that ALC-390 was strongly reacted with human gastric cancer cell line NUGC4-derived tumor tissue membrane component. This results show that NUGC4-derived tumor tissues contains the antigen recognized by ALC-390 in a large quantity.

(2) Preparation of ALC-390-binding Sepharose 4B gel

Ten milliliters of 1 mM hydrochloric acid was added to 1.25 g of Tresyl-activated Sepharose 4B (Pharmacia Fine Chemicals Inc.). After allowing the gel to swell at room temperature for 15 minutes, the gel was washed well with 250 ml of 1 mM hydrochloric acid on the glassfilter. Then, the gel was further washed well with 0.1M calcium hydrogencarbonate solution and 0.5M sodium chloride solution. A solution of ALC-390 which was obtained by dialysis against a solution containing 0.1M sodium hydrogencarbonate and 0.5M sodium chloride was added to a 5 ml portion of the gel so as to give a final concentration of 1 mg/ml. After reacting the mixture at room temperature for 4 hours, the gel was washed with 0.5M Tris-hydrochloride buffer (pH 8.0) and allowed to react in the same buffer for 3 hours. After completion of the reaction, the gel was washed with 0.5M sodium chloride-PBS to obtain ALC-390-binding Sepharose 4B gel. The content of ALC-390 in 1 ml of the gel was 4.72 mg.

(3) Solubilization of the antigen recognized by ALC-390 from the NUGC4-derived tumor tissue membrane component and Purification of the antigen using ALC-390-binding Sepharose 4B gel The NUGC4-derived tumor tissue membrane component (hereinafter referred to as NUGC4 tissue membrane component) was suspended in phosphate buffer (pH 7.2) to give a final concentration of 37 mg of protein/ml. To 300 of this suspension was added 4.5 ml of 0.1M diethylamine (pH 11.8) containing 0.34 mM octylglucoside (Calbiochem) and the mixture was stirred overnight at 4° C. to solubilize the membrane protein. Then, the mixture was centrifuged at 100,000×g for 30 minutes to separate the solubilized membrane protein from the other membrane components. To about 4.8 ml of the supernatant containing the membrane protein was added 15-fold volumes of phosphate buffer (pH 7.2) containing 0.34 mM octylglucoside and the membrane protein solution was adjusted to pH 7.2. About 77 ml of the membrane protein solution was filtered through a prefilter (SEPACOL MINI PP manufactured by Seikagaku Kogyo) and immediately after the filtration, the filtrate was applied to the column of ALC-390-binding Sepharose 4B gel (100 µl) for adsorption of the antigen. The column was washed well with PBS containing 0.34 mM octylglucoside and about 80 µl of the gel was recovered. To the gel were added 50 µl of PBS and 50 µl of a sample buffer [0.0625M Tris-hydrochloride buffer (pH 6.8) containing 2% SDS, 10% glycerol and 0.001% bromophenol blue] and the mixture was boiled at 100° C. for 5 minutes to extract ALC-390 and the antigen from the gel.

ALC-390-binding Sepharose 4B gel which did not adsorb NUGC4 tissue membrane component was also subjected to extraction with the sample buffer.

A 15 µl-portion of each extract was subjected to SDS-PAGE using 10% polyacrylamide gel and a dissociating buffer containing 0.025M Tris-hydroxymethylaminomethane, 0.192M glycine and 1% SDS (pH 8.3) in accordance with the method of Laemmli [Nature, 227, 680 (1970)]. For comparison, a solution of diethylamine (pH 11.5) containing 0.34 mM octylglucoside in which NUGC4 tissue membrane components were solubilized was boiled at 100° C. for 5 minutes in the sample buffer and subjected to SDS-PAGE. Electrophoresis was conducted at a constant electric current of 40 mA. After electrophoresis, the proteins were transferred to PVDF membrane from the polyacrylamide gel at an electric current of 2 mA/cm$^2$ in a transfer buffer using Transblot apparatus (manufactured by ATTO).

The PVDF membrane was subjected to protein staining with Coomassie brilliant blue and immunostaining with ALC-390 and normal mouse serum. The results are shown in FIG. 7.

As shown in FIG. 7A, two clear bands appear at the molecular weight of about 40K on lane 3 (treated with ALC-390-binding Sepharose 4B gel) as compared with Lane 1 (non-treated). From the results of the immunostaining with ALC-390 (FIG. 7C), it is found that this two bands strongly react with ALC-390 (lanes 3 and 4). On the other hand, the two bands did not react with normal mouse serum as shown in FIG. 7B. These results reveal that the two bands are the proteinous antigens recognized by ALC-390.

(4) Structure analysis of the proteinous antigens recognized by ALC-390

Among the bands of the proteinous antigens recognized by ALC-390 on lane 3 as shown in FIG. 7A, the band of most low molecular weight side was excised, put on the cartrigde for gas-phase sequencer (470A model, manufactured by ABI) and subjected to automatic Edman degradation. The thus-formed phenylthiohydantoin (PTH)-amino acid was determined using reversed-phase HPLC column (PTH-C18, 220×2.1 mm, particle size: 5 µm, manufactured by Brownney) equipped with On Line PTH analyzer (120A model, manufactured by ABI) by comparing with the retention volume of standard PTH-amino acid. As a result, the N-terminal amino acid sequence of the antigen was determined as follows.

```
1                        5                      10
Val—Leu—Glu—Val—Asp—Pro—Asn—Ile—Gln—Ala—
                        15                     20
Val—X—Thr—Gln—Glu—X—Glu—Gln—Ile—X—X—

(X : non-determined amino acid)
```

While the invention has been described in detail and with reference to specific embodiments thereof, it will be apparent to one skilled in the art that various changes and modifications can be made therein without departing from the spirit and scope thereof.

What is claimed is:

1. An antihuman pulmonary adenocarcinoma monoclonal antibody ALC-390 which is secreted by a hybridoma having the identifying characteristics of ECACC 87032601, belongs to the IgG class, and is reactive with membrane components of human pulmonary, adenocarcinoma cells and recognizes a surface protein within said membrane components as the antigen.

2. A method of detecting the presence of human pulmonary adenocarcinoma in a patient sample comprising;
    (a) subjecting a serum sample from the patient to an enzyme immunoassay with the monoclonal antibody of claim 1 and
    (b) examining the results for the presence of a positive reaction.

3. A diagnostic method of distinguishing human pulmonary adenocarcinoma cells from other cells including lung squamous cell carcinoma cells, lung large cell carcinoma cells, lung small cell carcinoma cells and normal human lung cells, said diagnostic method comprising the steps of:
    (a) subjecting a patient sample to an enzyme immunoassay with the monoclonal antibody of claim 1, and
    (b) assessing the degree of reactivity, if any, of the monoclonal antibody with the cells of the patient sample.

* * * * *